(12) United States Patent
Singhal

(10) Patent No.: US 8,460,700 B2
(45) Date of Patent: Jun. 11, 2013

(54) FIRST AID FORMULATIONS OF TURMERIC POWDER LAVENDER ESSENTIAL OIL AND GLYCERIN FOR DRESSING WOUNDS

(76) Inventor: Tara Chand Singhal, Torrance, CA (US)

( * ) Notice: Subject to any disclaimer, the term of this patent is extended or adjusted under 35 U.S.C. 154(b) by 330 days.

(21) Appl. No.: 12/590,359

(22) Filed: Nov. 5, 2009

(65) Prior Publication Data

US 2011/0104243 A1    May 5, 2011

(51) Int. Cl.
*A61K 9/14* (2006.01)
(52) U.S. Cl.
USPC .......................................... 424/446; 424/756
(58) Field of Classification Search
None
See application file for complete search history.

(56) References Cited

U.S. PATENT DOCUMENTS

| | | | | |
|---|---|---|---|---|
| 5,693,327 A | * | 12/1997 | Shah | 424/734 |
| 5,861,415 A | * | 1/1999 | Majeed et al. | 514/321 |
| 6,521,271 B1 | * | 2/2003 | Phan | 424/756 |
| 6,579,543 B1 | * | 6/2003 | McClung | 424/728 |
| 2007/0286908 A1 | * | 12/2007 | Clampitt | 424/680 |

FOREIGN PATENT DOCUMENTS

WO  WO 2007048171 A1 * 5/2007

OTHER PUBLICATIONS

"Stability of cyclosporine in an extemporaneously compounded paste," Ghnassia, L., et al., Am J Health-Syst Pharm 52: 2204-2207 (1995).*
Metric Converter (available at http://www.france-property-and-information.com/cooking_converter.htm).*

* cited by examiner

*Primary Examiner* — David J Blanchard
*Assistant Examiner* — Daniel F Coughlin
(74) *Attorney, Agent, or Firm* — Steve Roeder, Esq.

(57) ABSTRACT

A formulation made from natural substances, for healing cuts, bruises, wounds, and the like on the skin, has a natural-heal compound that has proportion of very fine *curcuma longa* (turmeric) powder, lavender essential oil, and glycerol that is compounded to the consistency of a paste. The formulation has ⅛ teaspoon to ⅜ teaspoon of very fine turmeric powder, one to three drops of lavender essential oil, and one-half to one and one-half drop of glycerol for a per square inch of the wound area. The formulation is used in a first aid means using a bandage, and as cotton gauze that is sealed in an air tight package.

17 Claims, 4 Drawing Sheets

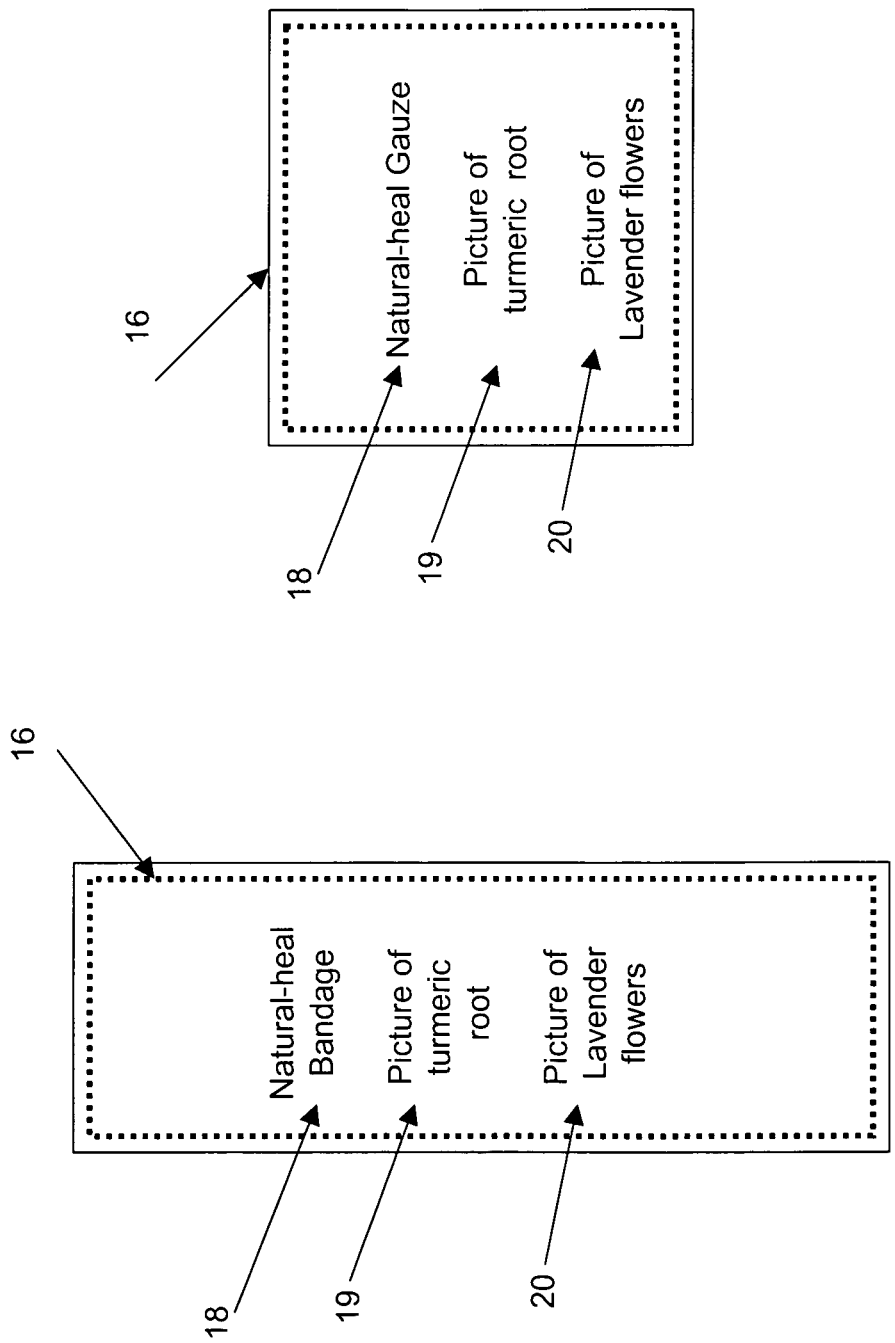

Preparing a natural-heal paste from mixing very very fine curcuma longa (turmeric) and lavender essential oil    30

Applying the natural-heal paste on a cotton gauze    32

Applying the gauze on the wound and then applying then a protective dressing    34

Mixing in the natural heal-paste a proportion of glycerol    36

Spreading, first the natural-heal paste on the wound applying, then the gauze before applying protective dressing    38

Sizing the wound area, using ¼ to ¾ tsp of turmeric, one to three drops of lavender, and one drop of glycerol for an inch of the skin area.    40

Figure 4

FIRST AID FORMULATIONS OF TURMERIC POWDER LAVENDER ESSENTIAL OIL AND GLYCERIN FOR DRESSING WOUNDS

CROSS REFERENCE

None.

FIELD OF THE INVENTION

Bandages, gauzes, and ointment that use formulation of *curcuma longa* (turmeric), lavender essential oil, and glycerol for healing wounds are described.

BACKGROUND

As researched from the world-wide-web, turmeric (*curcuma longa*) is widely known and has been widely researched in both the western world and in India for its many health benefits. In Ayurvedic medicine, turmeric is thought to have many medicinal properties and many in India use it as a readily available antiseptic for cuts, burns and bruises. Curcumin is the part of turmeric that provides turmeric with curcuminoids, which are believed to have health properties such as antioxidant, antibacterial and anti-inflammatory qualities.

The uses for lavender essential oil are many. For the skin, lavender helps abscesses, acne, allergies, athlete's feet and fungal infections, boils, bruises, burns, cold sores, cuts, dermatitis, eczema, hives, inflammations, insect bites and stings, lice, psoriasis, rashes, ringworm, scabies, scars, shingles-marks, sunburns and wounds.

Glycerin, also known as glycerol reduces or eliminates any skin disturbance, from psoriasis to bug bites or burns, cuts off pain and itching by quieting injured cells, doubles healing speed, and cuts scarring in half. The pure form of glycerin kills all bacteria on contact by instantly drawing the water out of them.

It is the objective of this preferred embodiment that, given the widely researched benefits of turmeric roots, lavender essential oil, and glycerin, first aid formulations of these natural substances would be highly beneficial for dressing wounds, thus providing a natural healing of the wounds without the use of chemically formulated antibiotics.

SUMMARY

A formulation made from natural substances, for healing cuts, bruises, burns and stings, wounds, and the like on the skin, has a natural-heal compound that has proportion of very fine *curcuma longa* (turmeric) powder and lavender essential oil that is compounded to the consistency of a paste. The natural-heal compound may also have a proportion of glycerol.

The formulation may be packaged as a bandage, a cotton-gauze and as an ointment tube. It is believed, the formulations of the preferred embodiments would supply the benefits of these natural substances, which have long been used separately for different purposes, for treating cuts, wounds and the like on the skin.

BRIEF DESCRIPTION OF THE DRAWINGS

Some of the novel features of this preferred embodiment will be best understood from the accompanying drawings, taken in conjunction with the accompanying description, in which similar reference characters refer to similar parts, and in which:

FIG. 3A-B is a block diagram that illustrates features of the present preferred embodiment of visual display of packaging.

FIG. 4 is a method diagram that illustrates features of the present preferred embodiment of natural-heal formulations.

DESCRIPTION

What is disclosed are formulations made from natural substances, for healing cuts, bruises, burns, stings, and wounds on the skin. In one embodiment, the formulation has a natural-heal compound that has a proportion of very fine *curcuma longa* (turmeric) powder and lavender essential oil that is compounded to the consistency of a paste. In another embodiment, the formulation has a natural-heal compound that has a proportion of very fine *curcuma longa* (turmeric) powder and glycerin, aka glycerol that is compounded to the consistency of a paste. In yet another embodiment, the formulation has a natural-heal compound that has a proportion of very fine *curcuma longa* (turmeric) powder, lavender essential oil and glycerol that is compounded to the consistency of a paste.

Turmeric has many medicinal properties and is used as a readily available antiseptic for cuts, burns and bruises by many in India. For the skin, lavender essential oil helps, bruises, burns, cuts, dermatitis, inflammations, insect bites and stings, rashes, sunburns and wounds. Glycerin, aka glycerol reduces or eliminates any skin disturbance, from psoriasis to bug bites or burns, cuts off pain and itching by quieting injured cells, doubles healing speed, and cuts scarring in half.

These benefits of turmeric roots, lavender essential oil, and glycerin make them suitable for first aid formulations of these natural substances that would be highly beneficial for dressing, thus providing a natural healing of the wounds without the use of chemically formulated antibacterial formulations.

In one embodiment, the formulation has ⅛ teaspoon to ⅜ teaspoon of very fine turmeric powder and one to three drops of lavender, for a per square inch of the skin area. In another embodiment, the formulation has ⅛ teaspoon to ⅜ teaspoon of turmeric and a half to a one and half drop of glycerol for a per square inch of the skin area. In yet another embodiment, the formulation has ⅛ teaspoon to ⅜ teaspoon of very fine turmeric powder, one to three drops of lavender essential oil, and a one-half to a one and one-half drop of glycerol for a per square inch of the skin area. These proportions are illustrative and may be slightly less or more than these proportions.

Figure 1:
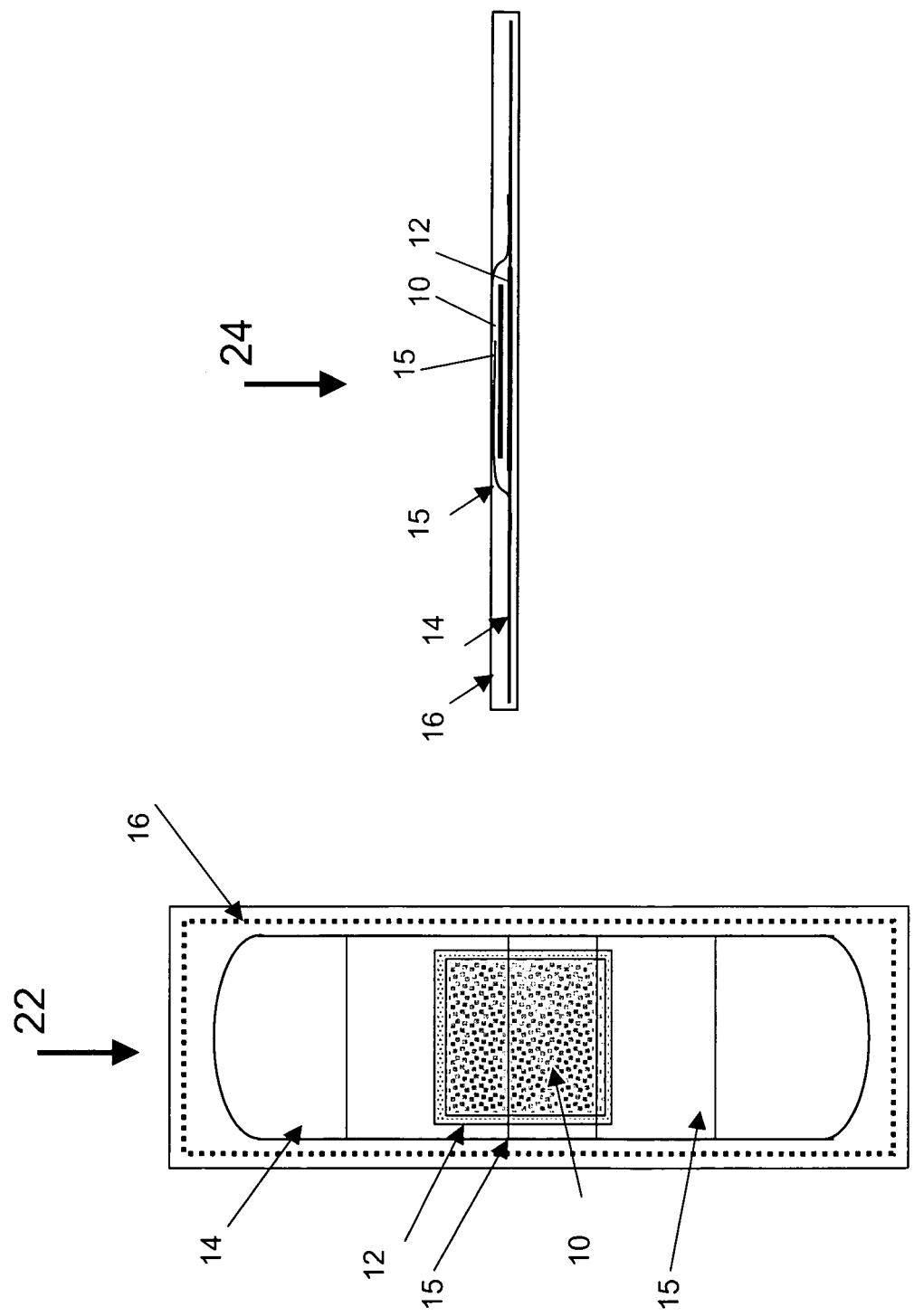
FIG. 1 is a block diagram that illustrates features of the present preferred embodiment of first aid means with natural-heal formulation.
Figure 2:
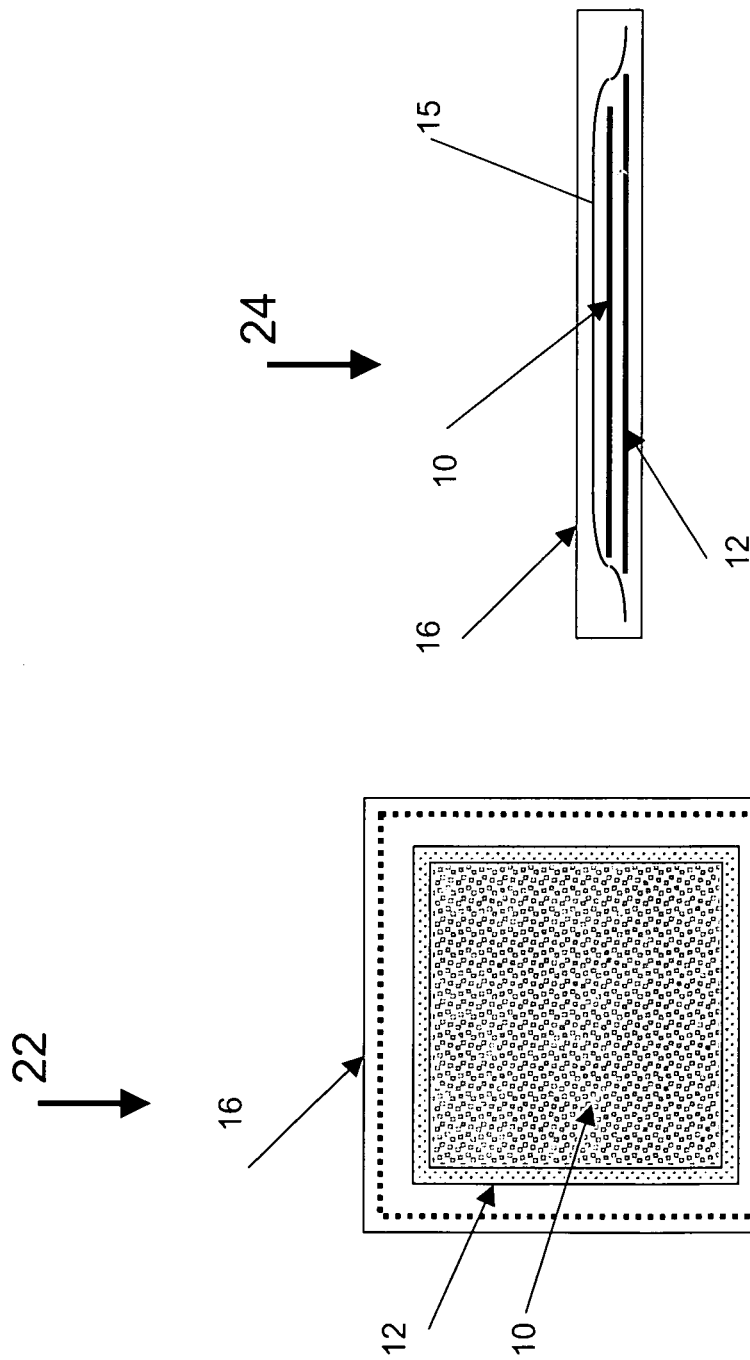
FIG. 2 is a block diagram that illustrates features of the present preferred embodiment of first aid means with natural-heal formulation.

The formulation is used in a first aid means using a bandage or cotton gauze that is sealed in an air tight package. As shown in FIG. 1, with a plan view 22 and a side view 24, the formulation is packaged in the form of a bandage 14. As shown in FIG. 2, the formulation is packaged onto gauze in the form of cotton gauze 12. Also, the packaging may also be in the form of tube (not shown).

As illustrated in FIG. 1, these formulations may be used in a first aid means in the form of a bandage 14, where the gauze 12 of the bandage 14 is spread with a layer of the natural-heal compound paste 10, becoming a nature-heal bandage for use in dressing cuts, bruises, and wounds on the skin.

The formulation in the form of bandage 14 may be packaged in an air-sealed package 16 for the natural-heal bandage as a first aid. When so packaged, two protective covers 15 protect the formulation 10 on the gauze surface.

A medical first aid means has a bandage 14, the gauze of the bandage is spread with a layer of the natural-heal formulation that is compounded from a proportion of very fine turmeric powder and a proportion of lavender essential oil, before being sealed in a package.

In a method of manufacture, the gauze 12 of the bandage 14 may be impregnated with the natural-heal compound 10 under pressure or being soaked over time. Alternatively, the formulation 10 may be spread as a layer on top of the gauze 12, before applying the protective flaps 15 and sealing the bandage 14 in air tight sealed package 16.

As shown in FIG. 2, with a plan view 22 and side view 24, the formulation may also have the packaging 16 as individually sealed cotton gauze 12, where the gauze 12 is spread with a layer of the formulation 10, before applying protective flaps 15, As illustrated in FIGS. 3A and 3B, the natural-heal bandage 18 has a bandage sealed package 16 that is identified with representations of the natural heal substances of turmeric and lavender essential oil. The representations of the natural heal substances of turmeric and lavender essential oil include pictures of roots of the turmeric plant 19 and flowers of the lavender plant 20. Such identifications help the purchaser and the user on being exposed with these identifications to understand the use of these natural substances for first aid. The public, in general, is interested is using as much as possible natural formulations derived from natural substances.

In commercial production, the formulation may be mixed in bulk quantities using similar proportions of the natural substances, turmeric powder, lavender essential oil and glycerol. The flexibility of the application of formulation on to the gauze in the process of manufacturing may be adjusted by adjusting the quantities of these substances.

Manufacturing techniques and machinery of manufacturing bandages, gauzes and tubes is prior art. These manufacturing methods are adapted to add the formulation of the embodiments herein. In one adaptation, the formulation 10 is applied to the gauze 12 by impregnating the gauze 12 under pressure. In another adaptation the formulation 10 is applied by spreading a layer of the formulation paste on to the gauze 12. There may be other similar methods of applying the formulation paste to the gauze and are not ruled out.

As illustrated with reference to FIG. 4, a method of natural healing wounds and cuts has the steps, where not all the steps may be used or used in the order specified.

At step 30, preparing a natural-heal paste from mixing very fine *curcuma longa* (turmeric) and lavender essential oil.

At step 32, applying the natural-heal paste on cotton gauze.

At step 34, applying the gauze on the wound and then applying a protective dressing.

At step 36, mixing in the natural heal-paste a proportion of glycerol.

At step 38, spreading, first the natural-heal paste on the wound; applying, then the gauze before applying protective dressing.

At step 40, sizing the wound area and using per square inch of the wound area, ⅛ to ⅜ teaspoon of very fine turmeric powder, one to three drops of lavender, and one-half to one and one-half drop of glycerol.

In summary, the preferred embodiment is on a natural-heal compound formulation that has turmeric powder and lavender and glycerol and is packaged as means for first aid using bandages, gauzes and ointment tubes. The benefits of these natural substances are well known and provide a natural heal approach for healing different types of skin problems, such as cuts, bruises, burns, stings, wounds, and the like.

While the particular preferred embodiment, as illustrated herein and disclosed in detail is fully capable of obtaining the objective and providing the advantages herein before stated, it is to be understood that it is merely illustrative of the presently preferred embodiments of the invention and that no limitations are intended to the details of construction or design herein shown other than as described in the appended claims.

What is claimed is:

1. A natural heal formulation, for application to cuts, bruises, burns, stings, and wounds on the skin, the formulation comprising:
   a. *curcuma longa* (turmeric) powder and
   b. lavender essential oil,
   wherein the turmeric powder and lavender essential oil are compounded to the consistency of a paste, and
   wherein the turmeric powder and lavender essential oil are the only natural heal substances in the formulation.

2. The formulation of claim 1, wherein
   the turmeric powder is present in an amount of from ¼ teaspoon to ¾ teaspoon and
   the lavender oil is present in an amount of from one to three drops, for application per square inch of skin area.

3. A first aid bandage or gauze for dressing cuts, bruises, and wounds on the skin, comprising:
   a. a sterile cotton gauze; and
   b. a layer of the formulation of claim 1 on a first side of the gauze.

4. A first aid bandage or gauze for dressing cuts, bruises, and wounds on the skin, comprising:
   a. a sterile cotton gauze; and
   b. a layer of the formulation of claim 2 on a first side of the gauze.

5. The first aid bandage or gauze of claim 3, wherein the bandage or gauze is packaged in an air-sealed package.

6. The formulation of claim 1, wherein the formulation is packaged in a squeezable tube.

7. A natural heal formulation, for application to cuts, bruises, burns, stings, and wounds on the skin, the formulation comprising:
   a. *curcuma longa* (turmeric) powder,
   b. lavender essential oil, and
   c. glycero,
   wherein the turmeric powder, lavender essential oil, and glycerol are compounded to the consistency of a paste, and
   wherein the turmeric powder and lavender essential oil are the only natural heal substances in the formulation.

8. The formulation of claim 7, wherein
   the turmeric powder is present in an amount of from ⅛ teaspoon to ⅜ teaspoon,
   the lavender oil is present in an amount of from one to three drops, and
   the glycerol is present in an amount of from one-half to one and one-half drop,
   for application per square inch of skin area.

9. A bandage or gauze for dressing cuts, bruises, and wounds on the skin, comprising:
   a. a sterile cotton gauze; and
   b. a layer of the formulation of claim 7 on a first side of the gauze.

10. A bandage or gauze for dressing cuts, bruises, and wounds on the skin, comprising:
    a. a sterile cotton gauze for dressing a wound; and
    b. a layer of the formulation of claim 8 on a first side of the gauze.

11. The bandage or gauze of claim 10, wherein the bandage or gauze is packaged in an air-sealed package.

12. The formulation of claim 7, wherein the formulation is packaged in a squeezable tube.

13. A formulation comprising natural heal substances, for application to cuts, bruises, burns, stings, and wounds on the skin, the formulation comprising:
   a. *curcuma longa* powder and
   b. glycerol,
   wherein the powder and glycerol are compounded to the consistency of a paste, and
   wherein the *curcuma longa* powder is the only natural heal substance in the formulation.

14. The formulation of claim 13, wherein
   the *curcuma longa* powder is present in an amount of from ⅛ teaspoon to ⅜ teaspoon and
   the glycerol is present in an amount of from one-half to one and one-half drop
   for application per square inch of skin area.

15. A bandage or gauze comprising:
   a. a sterile cotton gauze; and
   b. a layer of the formulation of claim 13 on a first side of the gauze.

16. A bandage or gauze comprising:
   a. a sterile cotton gauze for dressing a wound; and
   b. a layer of the formulation of claim 14 on a first side of the gauze.

17. The bandage or gauze of claim 16, wherein the bandage or gauze is packaged in an air-sealed package.

\* \* \* \* \*